(12) United States Patent
Gao et al.

(10) Patent No.: US 12,000,763 B2
(45) Date of Patent: Jun. 4, 2024

(54) DISPOSABLE BLOOD SAMPLER FOR BLOOD BRAID OF BLOOD BAG

(71) Applicant: TAIZHOU PEOPLE'S HOSPITAL, Jiangsu (CN)

(72) Inventors: Lingbao Gao, Jiangsu (CN); Yayun Sha, Jiangsu (CN); Ziang Gao, Jiangsu (CN)

(73) Assignee: TAIZHOU PEOPLE'S HOSPITAL, Jiangsu (CN)

( * ) Notice: Subject to any disclaimer, the term of this patent is extended or adjusted under 35 U.S.C. 154(b) by 488 days.

(21) Appl. No.: 17/286,412

(22) PCT Filed: Mar. 6, 2019

(86) PCT No.: PCT/CN2019/077102
§ 371 (c)(1),
(2) Date: Apr. 16, 2021

(87) PCT Pub. No.: WO2020/077937
PCT Pub. Date: Apr. 23, 2020

(65) Prior Publication Data
US 2021/0389215 A1 Dec. 16, 2021

(30) Foreign Application Priority Data
Oct. 18, 2018 (CN) .......................... 201811214998.X

(51) Int. Cl.
*G01N 1/10* (2006.01)
(52) U.S. Cl.
CPC ....... *G01N 1/10* (2013.01); *G01N 2001/1056* (2013.01)

(58) Field of Classification Search
USPC ..................................................... 73/863.81
See application file for complete search history.

(56) References Cited

U.S. PATENT DOCUMENTS 5,169,602 A * 12/1992 Pang .......................... A61J 1/20
422/538
5,270,003 A * 12/1993 Bernes ............. A61B 5/150366
604/905

FOREIGN PATENT DOCUMENTS

| CN | 104644437 A | | 5/2015 |
| CN | 108053878 A | * | 5/2018 |
| CN | 108126251 A | | 6/2018 |

(Continued)

*Primary Examiner* — Clayton E. LaBalle
*Assistant Examiner* — Warren K Fenwick
(74) *Attorney, Agent, or Firm* — Muncy, Geissler, Olds & Lowe, P.C.

(57) ABSTRACT

A disposable blood sampler for a blood braid of a blood bag includes a blood taking needle cannula, a threaded cannula, a blood braid clamp, a connecting pipe, a needle inserting sheet and a blood braid. The blood taking needle cannula includes a tubular threaded structure at both ends, a bottom port of the threaded cannula is connected with the blood taking needle cannula, and an upper port of the threaded cannula includes symmetrically distributed clamping slots extending to a middle lower part of the wall. Grips are arranged on the outer wall surface of the blood braid clamp, and the blood braid clamp is arranged in the threaded cannula. The grip is arranged outside the clamping slot, and the connecting pipe is directly inserted into the upper port. An inner cavity in which the needle inserting sheet is placed is arranged inside the inner part of the connecting pipe.

10 Claims, 3 Drawing Sheets

(56) References Cited

FOREIGN PATENT DOCUMENTS

| | | | |
|---|---|---|---|
| CN | 108279142 | A | 7/2018 |
| CN | 109260534 | A | 1/2019 |
| EP | 2813181 | A1 | 12/2014 |
| JP | 2004538104 | A * | 12/2004 |

* cited by examiner

DISPOSABLE BLOOD SAMPLER FOR BLOOD BRAID OF BLOOD BAG

TECHNICAL FIELD

The invention relates to the field of medical instruments, in particular to a disposable blood sampler for a blood braid of a blood bag.

BACKGROUND ART

In a medical blood sampler, the disposable blood sampler has the characteristics of being small in size, safe to use and convenient to operate, and is widely welcomed by medical staff and patients and extensively used in various medical institutions and diabetic patients at present.

At present, the law stipulates that a medical institution should perform a cross-matching test on a blood recipient and a blood donor before providing red blood cell therapy for clinical patients; and a blood donor sample is a small sealed braid for sample preservation after blood collection, and the blood braid is a slender plastic tube with a diameter of about 0.5 cm and a length of about 10-20 cm. Generally, in the cross-matching test, it is firstly cut along a front end of a next thermal bonding point by using scissors, and then the tail of the sample is cut, so that the blood flows into a test tube. During operation, blood samples in the braid often flow out or splash onto a workbench or a worker; at the same time, since the scissors used are in direct contact with the blood sample, the scissors are required to be sterilized once per bag of blood during the operation, or one pair of scissors is used for each sample. However, the blood sample processed every day is up to hundreds of bags, so that it is not feasible to use one pair of scissors for one bag of blood, and most medical institutions currently sterilize the scissors once for one use, or wipe the scissors with sterilizing liquid or soak the scissors with sterilizing liquid. In practice, cross-contamination is often caused because the disinfection time is too short to reach the effect of disinfection requirements. On the other hand, in the process of using scissors, potential damage to the body of workers is easily caused, and the chance of iatrogenic infection is increased.

In the past, more attention is paid to the blood collection effect in the design of such products. With the continuous progress of technology and the improvement of the living standard of people, the design concept of such products is that more attention is paid to use safety and user experience under the premise of ensuring the blood collection effect. Therefore, how to effectively solve the above problems is the subject of the present invention.

SUMMARY OF THE INVENTION

In order to solve the problems, the invention provides a disposable blood sampler for a blood braid of a blood bag, which is simple in structure and reasonable in design.

In order to achieve the above object, the technical solution adopted by the invention is as follows.

The invention relates to a disposable blood sampler for a blood braid of a blood bag, which is internally of a hollow structure and consists of a blood taking needle cannula, a threaded cannula, a blood braid clamp, a connecting pipe and a needle inserting sheet, wherein the blood taking needle cannula is of a threaded structure at both ends, a bottom port of the threaded cannula is connected with the blood taking needle cannula, and an upper port of the threaded cannula is provided with symmetrically distributed clamping slots extending to be close to the bottom of the wall; and symmetrical grips are arranged on the outer wall surface of the blood braid clamp, and the blood braid clamp is arranged in the threaded cannula; the grip can be arranged outside the clamping slot of the threaded cannula and can move up and down in the threaded cannula along the clamping slot; and the needle inserting sheet is connected with the threaded cannula by a connecting pipe, the connecting pipe can be directly inserted into the upper port of the threaded cannula, and an inner cavity in which the needle inserting sheet can be placed is arranged inside the connecting pipe, and a hollow needle is arranged on the needle inserting sheet.

The bottom port of the threaded cannula is of a threaded structure, and the bottom port is threadedly connected with the blood taking needle cannula.

The upper port of the threaded cannula is of a funnel-shaped structure, and a fixing plate and a protection plate are further arranged at the port; and when the connecting pipe is sleeved into the threaded cannula, the fixing plate fixes the connecting pipe, and the protection plate extends to the upper port of the wall of the connecting pipe, so that the hollow needle can be prevented from injuring fingers by mistake in the process of puncturing the blood braid.

The clamping slot is of a rectangular structure, and the width of the clamping slot does not exceed the width of the grip of the blood braid clamp.

The outer wall of the blood braid clamp is further provided with a V-shaped slot, the groove and the grip are distributed in a perpendicular state; and when the blood braid clamp is arranged in the clamping slot of the threaded cannula, the structure enables the blood braid clamp to clamp the blood braid by pressing the grip of the blood braid clamp, so that the blood braid can be driven to move up and down.

The needle inserting sheet is of an arc-shaped sheet structure and comprises a hollow needle, and the hollow needle is an L-shaped hollow needle bent at a right angle, and fixedly glued in the arc-shaped sheet body; and a sharp needle tip with an appropriate length is arranged at one end of the hollow needle, exposed out of the arc-shaped sheet body and perpendicular to the surface of the arc-shaped sheet, and the other hollow end of the hollow needle is flush with the arc-shaped sheet and is convenient to ventilate.

The connecting pipe further comprises a sealing cover, and the sealing cover is directly sleeved at the port of the connecting pipe.

The blood taking needle cannula is a cannula with double threads, one end of the blood taking needle cannula is threadedly connected with the threaded cannula, and the other end of the blood taking needle cannula is threadedly connected with a plug of a test tube.

Preferably, the inner diameter of the threaded cannula is slightly larger than the outer diameter of the blood braid.

Preferably, grips are symmetrically distributed on the outer wall of the blood braid clamp, and the grip part of the blood braid clamp is pressed to enable the blood braid clamp to move up and down the threaded cannula along symmetrically distributed openings.

The invention has the following beneficial effects.

According to the invention, a brand-new cannula structure which is used for placing the blood braid inside the blood sampling cannula and is matched with the blood sampling threaded cannula is adopted, so that the blood collection work can be timely, safely and effectively carried out without a method of shearing the blood braid by using scissors.

The bottom port of the threaded cannula is of a threaded structure, the bottom port is threadedly connected with one end of the blood taking needle cannula, so that the blood taking needle is well fixed, and the puncturing the blood braid is operated conveniently; in addition, the other end of the blood taking needle cannula is threadedly connected with the plug of the blood taking test tube, and the sealing performance is good.

The clamping slot is of a rectangular structure, the width of the clamping slot does not exceed the width of the grip of the blood braid clamp, the outer wall of the blood braid clamp is further provided with a V-shaped slot, and the clamping slot and the grip are distributed in a perpendicular state; and when the blood braid clamp is arranged in the clamping slot of the threaded cannula, the grip is positioned just outside the clamping slot of the threaded cannula, and the structure enables the blood braid clamp to clamp the blood braid by pressing the grip of the blood braid clamp, so that the blood braid can be driven to move up and down. This structure is applicable to blood braids of various lengths, and can quickly enable the blood taking needle on the blood taking needle cannula to accurately puncture the blood braid.

The needle inserting sheet is of an arc-shaped sheet structure and comprises a hollow needle, and the hollow needle is arranged on a needle hole in the inner wall of the needle inserting sheet; an arc-shaped cannula sheet is arranged at the upper port of the threaded cannula, the length of the arc-shaped cannula sheet extends to the relative position of the hollow needle, and fingers can be effectively prevented from being punctured when the needle punctures the blood braid.

Due to the fact that the limiting protrusion is arranged on the needle inserting sheet, the needle inserting sheet can be effectively prevented from rotating in the connecting pipe by being matched with the limiting groove on the connecting pipe.

The blood taking device further comprises a sealing cover, and the sealing cover is directly sleeved at the port of the connecting pipe, so that the contact between bacteria in air and blood is avoided, and the invention is clean and sanitary.

BRIEF DESCRIPTION OF THE DRAWINGS

The invention is further described below with reference to the accompanying drawings.

1—blood taking needle cannula; 2—threaded cannula; 3—blood braid clamp; 4—connecting pipe; 5—needle inserting sheet; 6—blood braid; 7—sealing cover; 11—blood taking needle; 22—clamping slot; 23—upper port of threaded cannula; 24—fixing plate; 25—protection plate; 33—grip; 34—V-shaped slot; 44—inner cavity; 45—blood braid pipeline; 46—placement slot for needle inserting sheet; 47—placement slot notch; 48—limiting protrusion; 49—limiting slot; 55—needling instrument slot; 56—limiting groove; and 57—hollow needle.

DETAILED DESCRIPTION OF THE INVENTION

The invention will be further described with reference to the drawings.

Embodiment 1

Figure 1:
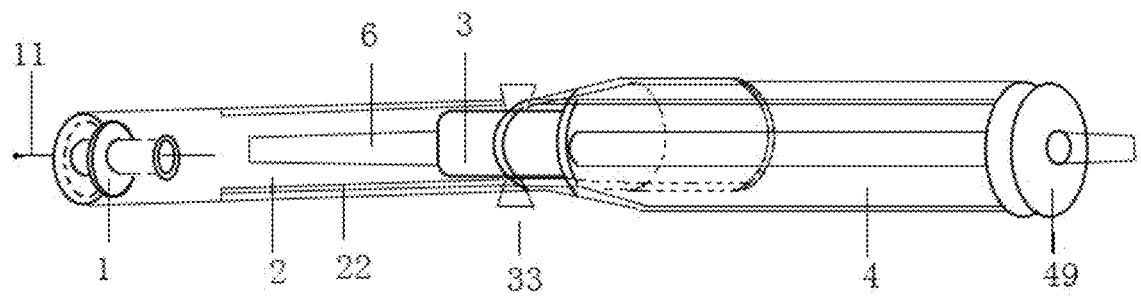
FIG. 1 is a schematic view of a disposable blood sampler for a blood braid of a blood bag.
Figure 2:
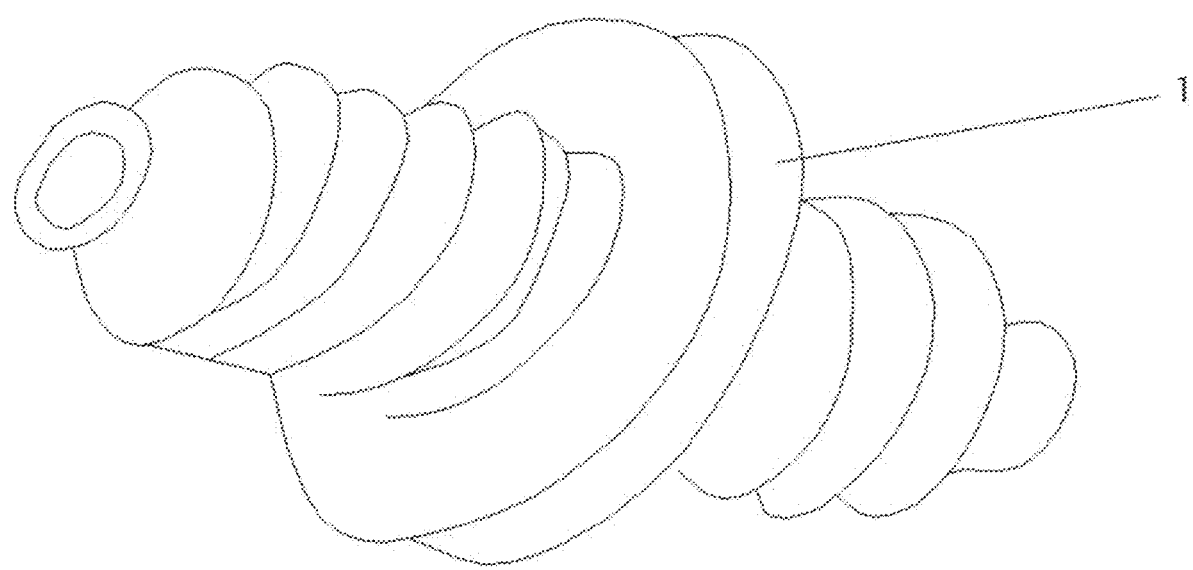
FIG. 2 is a structurally schematic view of a blood taking needle cannula.
Figure 3:
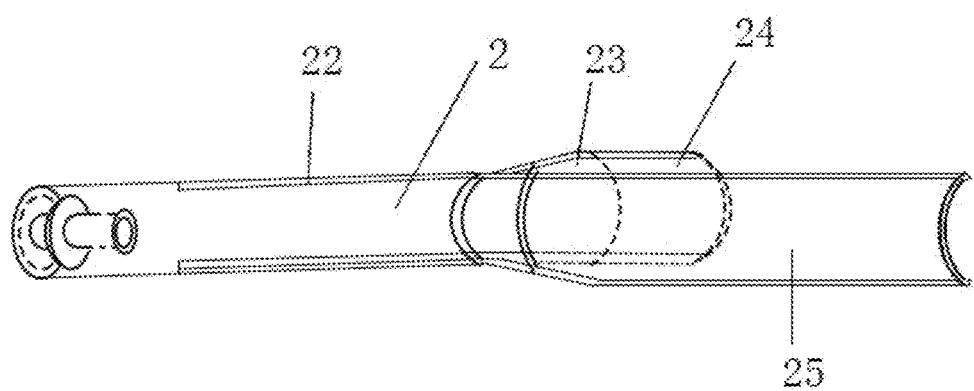
FIG. 3 is a structurally schematic view of a threaded cannula.
Figure 4:
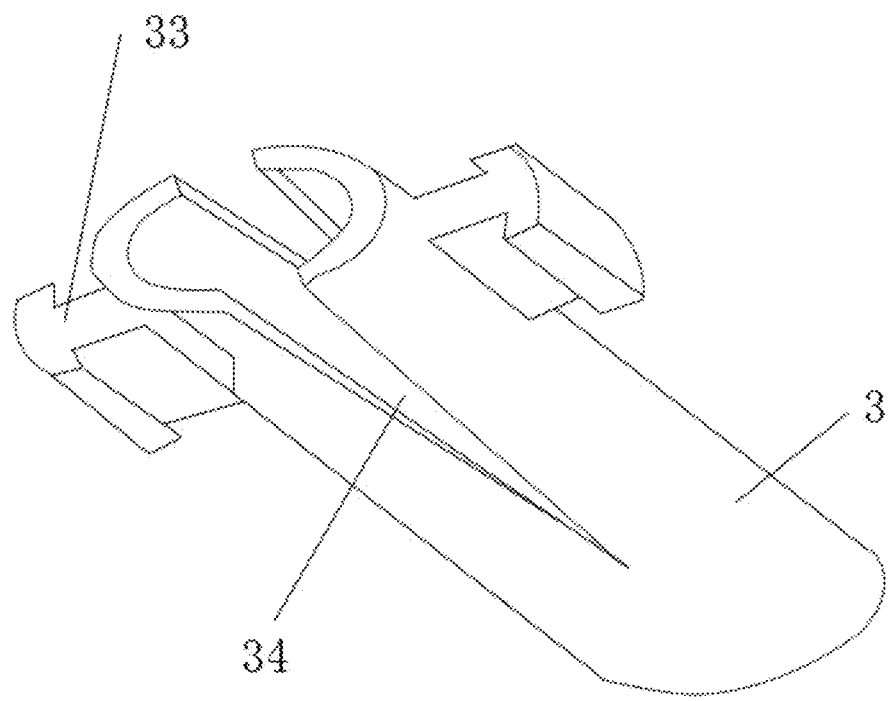
FIG. 4 is a structurally schematic view of a blood braid clamp.
Figure 5:
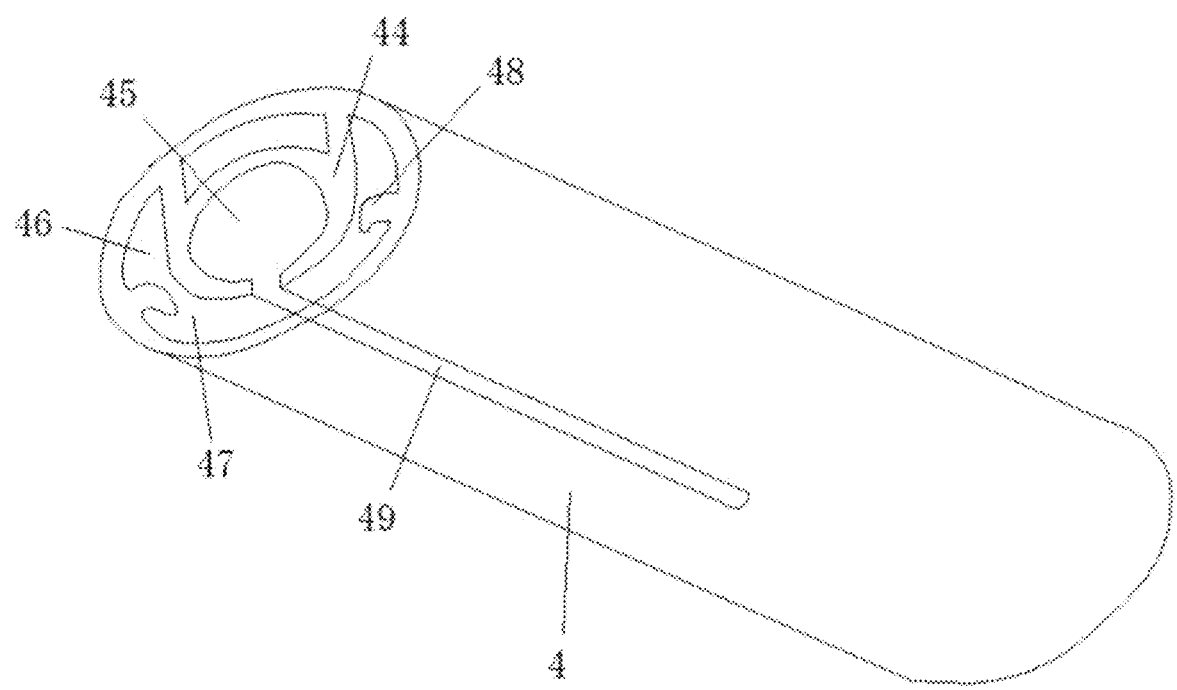
FIG. 5 is a structurally schematic view of a connecting pipe.
Figure 6:
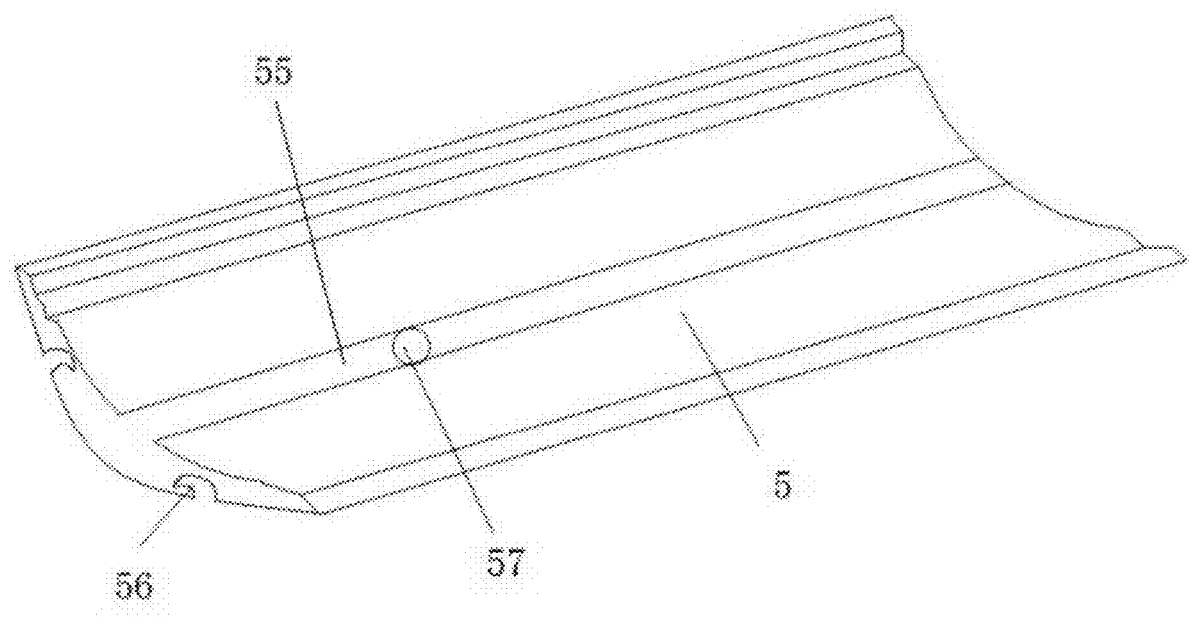
FIG. 6 is a structurally schematic view of a needle inserting sheet.
Figure 7:
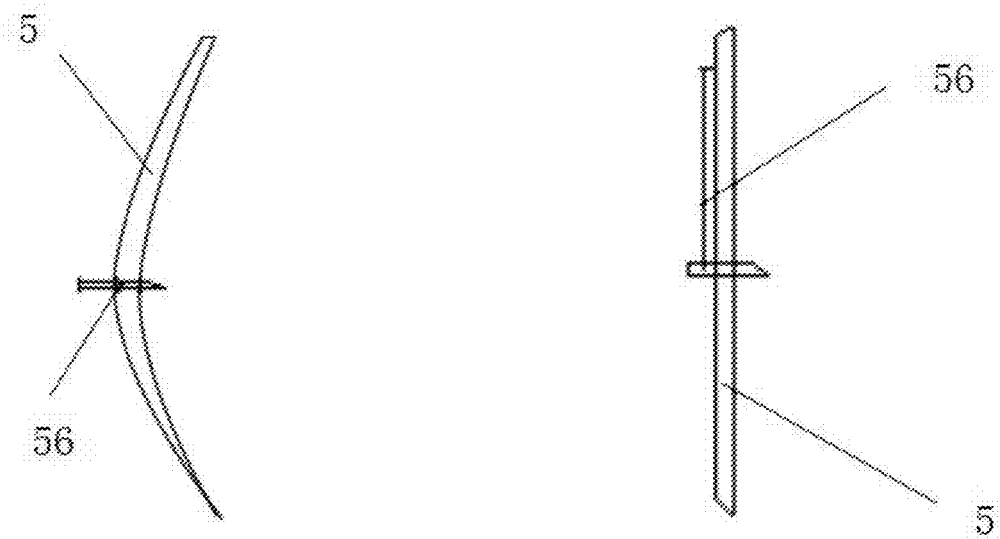
FIG. 7 is a structurally schematic view of a hollow needle and the needle inserting sheet.

As shown in FIG. 1, the invention provides a disposable blood sampler for a blood braid of a blood bag, which comprises a blood taking needle cannula 1, a threaded cannula 2, a blood braid clamp 3, a connecting pipe 4, a needle inserting sheet 5 and a blood braid 6, wherein the blood taking needle cannula 1 is of a threaded structure at both ends, the threaded cannula 2 is of a tubular structure, a bottom port of the threaded cannula 2 is connected with the blood taking needle cannula 1, and an upper port of the threaded cannula 2 is provided with symmetrically distributed clamping slots 22 extending to a middle lower part of the wall; symmetrical grips 33 are arranged on the outer wall surface of the blood braid clamp 3, and the blood braid clamp 3 is arranged in the threaded cannula 2; the grip 33 can be positioned outside the clamping slot 22 of the threaded cannula 2 and can move up and down in the threaded cannula 2 along the clamping slot 22; and the needle inserting sheet 5 is connected with the threaded cannula 2 by a connecting pipe 4, and the connecting pipe 4 can be directly inserted into the upper port of the threaded cannula 2; and the inner cavity 44 in which the needle inserting sheet 5 can be placed is arranged inside the connecting pipe 4, and the needle inserting sheet 5 is provided with a needling instrument slot 55.

The bottom port of the threaded cannula 2 is of a threaded structure, and the bottom port is threadedly connected with the blood taking needle cannula 1.

The upper port 23 of the threaded cannula 2 is of a funnel-shaped structure, a fixing plate 24 and a protection plate 25 are further arranged at the port, and the fixing plate 24 and the protection plate 25 are integrally formed with the upper port 23 of the threaded cannula 2; and when the connecting pipe 4 is sleeved in the threaded cannula 2, the fixing plate 24 fixes the connecting pipe 4, and the protection plate 25 extends to an upper port of the wall of the connecting pipe 4.

The clamping slot 22 is of a rectangular structure, and the width of the clamping slot 22 does not exceed the width of the grip 33 of the blood braid clamp 3; and the grip 33 is of a T-shaped structure or a trapezoid structure and integrally formed with and the blood braid clamp 3.

The outer wall of the blood braid clamp 3 is further provided with a V-shaped slot 34, and the V-shaped slot 34 and the grip 33 are distributed in a perpendicular state; and when the blood braid clamp 3 is arranged in the clamping slot 22 of the threaded cannula 2, the structure enables the blood braid clamp 3 to clamp the blood braid 6 by pressing the grip 33 of the blood braid clamp 3, so that the blood braid 6 can be driven to move up and down.

The inner cavity 44 of the connecting pipe 4 is provided with a blood braid pipeline 45, the diameter of the blood braid pipeline is slightly larger than the diameter of the blood braid, the blood braid pipeline 45 and the connecting pipe 4 are of a concentric circle structure; a placement slot 46 for a needle inserting sheet for placing the needle inserting sheet 5 is arranged between the blood braid pipeline 45 and the inner wall of the connecting pipe 4, and the placement slot 46 for the needle inserting sheet is of an arc-shaped structure; a limiting slot 49 is arranged at the center of the placement slot 46 for the needle inserting sheet and communicated with the placement slot 46 for the needle inserting sheet and the blood braid pipeline 45; and a limiting protrusion 48 is arranged at a placement slot notch 47 of the placement slot 46 for the needle inserting sheet, and the limiting protrusions are two, and can be rectangular and circular limiting protrusions or protrusions which are opposite to each other and form a certain angle.

The needle inserting sheet 5 is of an arc-shaped sheet structure and comprises a needling instrument slot 55, a limiting groove 56 and a hollow needle 57, wherein the needling instrument slot 55 is arranged on the central inner wall of the needle inserting sheet 5; the hollow needle 57 is arranged in the needling instrument slot 55, one end of the hollow needle 57 protrudes out of the inner wall of the needle inserting sheet 5 and is perpendicular to the interior of the needle inserting sheet 5, and the other end of the hollow needle 57 may be fixedly adhered to the needle inserting sheet 5; and other medical needles may be used with the hollow needle 5.

The blood taking needle cannula 1 is a cannula with double threads, a blood taking needle 11 is arranged on and penetrates through the blood taking needle cannula 1, one end of the blood taking needle cannula 1 is threadedly connected with the threaded cannula 2, and the other end of the blood taking needle cannula 1 is threadedly connected with a plug of a test tube.

The needle inserting sheet 5 further comprises a limiting groove 56 matched with the structural shape of the limiting protrusion 48, and the limiting protrusion 48 is matched with the limiting groove 56; and when the needle inserting sheet 5 is placed in the connecting pipe 4, the needle inserting sheet 5 cannot rotate in the connecting pipe 4.

Preferably, the inner diameter of the threaded cannula 2 is slightly larger than the outer diameter of the blood braid.

Preferably, grips 33 are symmetrically distributed on the outer wall of the blood braid clamp 3, and the grip 33 part of the blood braid clamp is pressed to enable the blood braid clamp 3 to move up and down the threaded cannula 2 along the symmetrically arranged clamping slots 22 of the threaded cannula 2.

An orifice of the connecting pipe 4 further comprises a sealing cover 7, the orifice of the connecting pipe (4) can be directly sleeved in the sealing cover 7, and the port of the connecting pipe 4 is fixedly glued with the sealing cover 7.

As a preferred embodiment, the hollow needle 57 is sleeved with a protection sheath, and the structure of the protection sheath can be matched according to the structural design of the hollow needle 57 so as to prevent the needle tip from puncturing the inner wall of the connecting pipe during transportation and injuring fingers by mistake.

Embodiment 2

Different from Embodiment 1, an upper part of the threaded cannula 2 is provided with symmetrically distributed clamping slots 22 extending to be close to the bottom of the wall; and the clamping slot 22 of the grip 33 is of an elliptical structure, the width of the clamping slot 22 does not exceed the width of the grip of the blood braid clamp, and the grip 33 is of a trapezoidal structure.

The operating principle of the invention is as follows.

1. The blood braid clamp 3 is inserted into the clamping slot 22 of the threaded cannula 2 along the direction of the clamping slot 22 from the upper port of the threaded cannula 2, the two blood braid grips 33 are positioned outside the threaded cannula 2, and the blood braid grip 33 is pressed to slide the blood braid placed therein up and down.

2. The needle inserting sheet fixed with a sharp needling instrument is inserted into the connecting pipe, so that the limiting protrusion 48 is matched with the limiting groove 56.

3. The connecting pipe 4 is placed into a port at the upper end of the threaded cannula 2;

4. The sealing cover 7 is covered and fixed at the upper end of the connecting pipe 4;

5. The upper end of the blood taking needle cannula 1 with the hollow needle is fixed to the center of the lower end of the threaded cannula 2.

6. The lower end of the blood taking needle cannula 1 is fixedly connected with a sealing plug of the blood taking cannula, the blood braid is just moved downwards from right above the blood taking needle cannula by pressing the grip 33, so that the blood taking needle just punctures the blood braid; on the other hand, the connecting pipe is rotated so that the hollow needle on the needle inserting sheet can just puncture the side wall of the blood braid; and working along both lines, the blood in the blood braid flows into the blood taking cannula to complete the process.

The invention claimed is:

1. A disposable blood sampler for a blood braid of a blood bag comprising a blood taking needle cannula, a threaded cannula, a blood braid clamp, a connecting pipe and a needle inserting sheet, wherein the blood taking needle cannula is of a threaded structure at both ends, the threaded cannula is of a tubular structure, a bottom port of the threaded cannula is connected with the blood taking needle cannula, and an upper port of the threaded cannula is provided with symmetrically distributed clamping slots extending to a middle lower part of a wall; symmetrical grips are arranged on an outer surface of a wall of the blood braid clamp, and the blood braid clamp is arranged in the threaded cannula; the symmetrical grips are positioned outside the clamping slot of the threaded cannula, and the blood braid clamp moves up and down in the threaded cannula along the clamping slot; and the connecting pipe is inserted into the upper port of the threaded cannula, an inner cavity in which the needle inserting sheet can be placed is arranged inside the connecting pipe, and the needle inserting sheet is of an arc-shaped sheet structure.

2. The disposable blood sampler for a blood braid of a blood bag according to claim 1, wherein the inner cavity of the connecting pipe is of a hollow structure, a blood braid pipeline is arranged in the inner cavity, and the blood braid pipeline and the connecting pipe are of a concentric circle structure; a placement slot for the needle inserting sheet for placing the needle inserting sheet is arranged between the blood braid pipeline and an inner wall of the connecting pipe, and the placement slot for the needle inserting sheet is of an arc-shaped structure; a limiting slot is arranged at a center of the placement slot for the needle inserting sheet and communicating with the placement slot for the needle inserting sheet and the blood braid pipeline; and the placement slot for the needle inserting sheet comprises a limiting protrusion arranged at a placement slot notch of the placement slot for the needle inserting sheet.

3. The disposable blood sampler for a blood braid of a blood bag according to claim 1, wherein the clamping slot is of a rectangular structure or an elliptical structure, a width of the clamping slot does not exceed a width of the symmetrical grips of the blood braid clamp, the clamping slot extends to a bottom of the wall of the blood braid clamp, and the symmetrical grips are of a T-shaped structure or a trapezoid structure and integrally formed with the blood braid clamp.

4. The disposable blood sampler for a blood braid of a blood bag according to claim 1, wherein the upper port of the threaded cannula is of a funnel-shaped structure, a fixing plate and a protection plate are further arranged at the upper port, and the fixing plate and the protection plate are integrally formed with the upper port of the threaded cannula; and when the connecting pipe is sleeved in the threaded cannula, the fixing plate fixes the connecting pipe, and the protection plate extends to an upper port of the wall of the connecting pipe.

5. The disposable blood sampler for a blood braid of a blood bag according to claim 1, wherein the wall of the blood braid clamp is further provided with symmetrically distributed V-shaped slots, and the V-shaped slots and the symmetrical grips are distributed in a perpendicular state.

6. The disposable blood sampler for a blood braid of a blood bag according to claim 1, wherein the needle inserting sheet comprises a needling instrument slot, a limiting groove and a hollow needle, the hollow needle is sleeved with a protection sheath, a structure of the protection sheath is matched with that of the hollow needle, and the needling instrument slot is arranged on a center of an inner wall of the needle inserting sheet; the hollow needle is an L-shaped hollow needle bent at a right angle, and is fixed in the needling instrument slot by gluing, one end of the hollow needle protrudes out of the inner wall of the needle inserting sheet and is perpendicular to an interior of the needle inserting sheet, and an other end of the hollow needle is fixedly adhered to the needle inserting sheet; the placement slot for the needle inserting sheet comprises a limiting protrusion arranged at a placement slot notch of the placement slot for the needle inserting sheet, and the needle inserting sheet further comprises a limiting groove matched with a structural shape of the limiting protrusion.

7. The disposable blood sampler for a blood braid of a blood bag according to claim 1, wherein the blood taking needle cannula is a cannula with double threads, a blood taking needle is arranged on and penetrates through the blood taking needle cannula, one end of the blood taking needle cannula is threadedly connected with the threaded cannula, and an other end of the blood taking needle cannula is threadedly connected with a plug of a test tube.

8. The disposable blood sampler for a blood braid of a blood bag according to claim 1, wherein the placement slot for the needle inserting sheet comprises two limiting protrusions, the two limiting protrusions are in rectangular shape or circular shape, and are opposite to each other.

9. The disposable blood sampler for a blood braid of a blood bag according to claim 1, wherein the bottom port of the threaded cannula is of a threaded structure, and the bottom port of the threaded cannula is threadedly connected with one end of the blood taking needle cannula.

10. The disposable blood sampler for a blood braid of a blood bag according to claim 1, wherein an orifice of the connecting pipe further comprises a sealing cover, the orifice of the connecting pipe is directly sleeved in the sealing cover, and a port of the connecting pipe is fixedly glued with the sealing cover.

\* \* \* \* \*